(12) United States Patent
Yang et al.

(10) Patent No.: US 7,160,679 B1
(45) Date of Patent: Jan. 9, 2007

(54) METHOD OF DIAGNOSING, MONITORING, AND STAGING LUNG CANCER

(75) Inventors: Fei Yang, San Diego, CA (US); Roberto A. Macina, San Jose, CA (US); Yongming Sun, San Jose, CA (US)

(73) Assignee: diaDexus, Inc., South San Francisco, CA (US)

( * ) Notice: Subject to any disclaimer, the term of this patent is extended or adjusted under 35 U.S.C. 154(b) by 0 days.

(21) Appl. No.: 09/700,770

(22) PCT Filed: May 12, 1999

(86) PCT No.: PCT/US99/10344

§ 371 (c)(1),
(2), (4) Date: Jan. 16, 2001

(87) PCT Pub. No.: WO99/60160

PCT Pub. Date: Nov. 25, 1999

Related U.S. Application Data

(60) Provisional application No. 60/086,212, filed on May 21, 1998.

(51) Int. Cl.
*C12Q 1/68* (2006.01)
(52) U.S. Cl. .......................................... 435/6
(58) Field of Classification Search ................. 435/7.1; 436/6.4
See application file for complete search history.

(56) References Cited

U.S. PATENT DOCUMENTS

| | | | |
|---|---|---|---|
| 5,939,265 A * | 8/1999 | Cohen et al. | |
| 6,203,979 B1 * | 3/2001 | Bandman et al. | |
| 6,331,427 B1 | 12/2001 | Robison | ................... 435/226 |
| 2002/0103125 A1 | 8/2002 | Ashkenazi | |
| 2002/0123463 A1 | 9/2002 | Ashkenazi | |
| 2002/0127576 A1 | 9/2002 | Ashkenazi | |
| 2002/0132252 A1 | 9/2002 | Ashkenazi | |
| 2002/0142961 A1 | 10/2002 | Ashkenazi | |
| 2002/0160384 A1 | 10/2002 | Ashkenazi | |
| 2002/0177164 A1 | 11/2002 | Ashkenazi | |
| 2002/0193299 A1 | 12/2002 | Ashkenazi | |
| 2002/0193300 A1 | 12/2002 | Ashkenazi | |
| 2002/0197615 A1 | 12/2002 | Ashkenazi | |
| 2003/0003531 A1 | 1/2003 | Ashkenazi | |
| 2003/0008297 A1 | 1/2003 | Ashkenazi | |
| 2003/0017476 A1 | 1/2003 | Ashkenazi | |
| 2003/0017981 A1 | 1/2003 | Ashkenazi | |
| 2003/0017982 A1 | 1/2003 | Ashkenazi | |
| 2003/0022187 A1 | 1/2003 | Ashkenazi | |
| 2003/0027162 A1 | 2/2003 | Ashkenazi | |
| 2003/0027163 A1 | 2/2003 | Ashkenazi | |
| 2003/0027985 A1 | 2/2003 | Ashkenazi | |
| 2003/0027992 A1 | 2/2003 | Eaton | |
| 2003/0032023 A1 | 2/2003 | Ashkenazi | |
| 2003/0040072 A1 | 2/2003 | Baker | |
| 2003/0040078 A1 | 2/2003 | Baker | |
| 2003/0040473 A1 | 2/2003 | Ashkenazi | |
| 2003/0044806 A1 | 3/2003 | Ashkenazi | |
| 2003/0044928 A1 | 3/2003 | Baker | |
| 2003/0049638 A1 | 3/2003 | Ashkenazi | |
| 2003/0049735 A1 | 3/2003 | Eaton | |
| 2003/0049752 A1 | 3/2003 | Baker | |
| 2003/0049755 A1 | 3/2003 | Baker | |
| 2003/0049764 A1 | 3/2003 | Baker | |
| 2003/0049783 A1 | 3/2003 | Baker | |
| 2003/0050462 A1 | 3/2003 | Eaton | |
| 2003/0050465 A1 | 3/2003 | Eaton | |
| 2003/0054359 A1 | 3/2003 | Ashkenazi | |
| 2003/0054403 A1 | 3/2003 | Ashkenazi | |
| 2003/0054404 A1 | 3/2003 | Ashkenazi | |
| 2003/0054459 A1 | 3/2003 | Baker | |
| 2003/0054464 A1 | 3/2003 | Baker | |
| 2003/0054465 A1 | 3/2003 | Baker | |
| 2003/0054469 A1 | 3/2003 | Baker | |
| 2003/0054472 A1 | 3/2003 | Baker | |
| 2003/0054473 A1 | 3/2003 | Baker | |
| 2003/0054480 A1 | 3/2003 | Baker | |
| 2003/0054987 A1 | 3/2003 | Ashkenazi | |
| 2003/0055222 A1 | 3/2003 | Eaton | |
| 2003/0059780 A1 | 3/2003 | Ashkenazi | |
| 2003/0059782 A1 | 3/2003 | Ashkenazi | |
| 2003/0059783 A1 | 3/2003 | Ashkenazi | |
| 2003/0059831 A1 | 3/2003 | Ashkenazi | |
| 2003/0059832 A1 | 3/2003 | Ashkenazi | |
| 2003/0059833 A1 | 3/2003 | Ashkenazi | |
| 2003/0060407 A1 | 3/2003 | Ashkenazi | |
| 2003/0060600 A1 | 3/2003 | Eaton | |
| 2003/0064443 A1 | 4/2003 | Baker | |
| 2003/0064448 A1 | 4/2003 | Baker | |
| 2003/0064449 A1 | 4/2003 | Baker | |
| 2003/0064463 A1 | 4/2003 | Baker | |
| 2003/0065161 A1 | 4/2003 | Eaton | |

(Continued)

FOREIGN PATENT DOCUMENTS

EP    1033401 A2    9/2000

(Continued)

OTHER PUBLICATIONS

Larsson A, Henriksson G, Manthorpe R, Sallmyr A, Bredberg A. Scand J Immunol Sep. 2001;54(3):328-34.*

(Continued)

*Primary Examiner*—Christopher H. Yaen
(74) *Attorney, Agent, or Firm*—Licata & Tyrrell P.C.; Nathan P. Letts

(57) ABSTRACT

The present invention provides a new method for detecting, diagnosing, monitoring, staging, and prognosticating lung cancer.

17 Claims, No Drawings

U.S. PATENT DOCUMENTS

| | | |
|---|---|---|
| 2003/0068623 A1 | 4/2003 | Ashkenazi |
| 2003/0068680 A1 | 4/2003 | Baker |
| 2003/0068688 A1 | 4/2003 | Baker |
| 2003/0068708 A1 | 4/2003 | Baker |
| 2003/0068713 A1 | 4/2003 | Baker |
| 2003/0068723 A1 | 4/2003 | Baker |
| 2003/0068737 A1 | 4/2003 | Baker |
| 2003/0068761 A1 | 4/2003 | Baker |
| 2003/0068762 A1 | 4/2003 | Baker |
| 2003/0068769 A1 | 4/2003 | Baker |
| 2003/0068771 A1 | 4/2003 | Baker |
| 2003/0069394 A1 | 4/2003 | Eaton |
| 2003/0073090 A1 | 4/2003 | Ashkenazi |
| 2003/0073173 A1 | 4/2003 | Baker |
| 2003/0073179 A1 | 4/2003 | Baker |
| 2003/0073180 A1 | 4/2003 | Baker |
| 2003/0073181 A1 | 4/2003 | Baker |
| 2003/0073183 A1 | 4/2003 | Baker |
| 2003/0073185 A1 | 4/2003 | Baker |
| 2003/0082717 A1 | 5/2003 | Baker |
| 2003/0082767 A1 | 5/2003 | Baker |
| 2003/0083461 A1 | 5/2003 | Ashkenazi |
| 2003/0083473 A1 | 5/2003 | Eaton |
| 2003/0087374 A1 | 5/2003 | Baker |
| 2003/0087376 A1 | 5/2003 | Baker |
| 2003/0092121 A1 | 5/2003 | Baker |
| 2003/0096351 A1 | 5/2003 | Baker |
| 2003/0096353 A1 | 5/2003 | Baker |
| 2003/0096357 A1 | 5/2003 | Baker |
| 2003/0096358 A1 | 5/2003 | Baker |
| 2003/0096359 A1 | 5/2003 | Baker |
| 2003/0100061 A1 | 5/2003 | Baker |
| 2003/0104538 A1 | 6/2003 | Baker |
| 2003/0104544 A1 | 6/2003 | Baker |
| 2003/0104545 A1 | 6/2003 | Baker |
| 2003/0104547 A1 | 6/2003 | Baker |
| 2003/0104548 A1 | 6/2003 | Baker |

FOREIGN PATENT DOCUMENTS

| | | |
|---|---|---|
| WO | WO 96/39419 | 12/1996 |
| WO | WO 98/11236 A1 | 3/1998 |
| WO | WO 98/13484 | 4/1998 |
| WO | WO 98/13484 A1 | 4/1998 |
| WO | WO 98/20143 A1 | 5/1998 |
| WO | WO 98/20143 A1 | 5/1998 |
| WO | WO 98/22597 A2 | 5/1998 |
| WO | WO 98/33926 A1 | 8/1998 |
| WO | WO 98/33926 A1 | 8/1998 |
| WO | WO 98/45437 | 10/1998 |
| WO | WO 99/06439 A2 | 2/1999 |
| WO | WO 99/33869 | 7/1999 |
| WO | WO 99/36550 * | 7/1999 |
| WO | WO 99/36550 A2 | 7/1999 |
| WO | WO 99/60160 | 11/1999 |
| WO | WO 99/60160 A1 | 11/1999 |
| WO | WO 99/63088 | 12/1999 |
| WO | WO 00/00610 | 1/2000 |
| WO | WO 00/01821 | 1/2000 |
| WO | WO 00/04137 A1 | 1/2000 |
| WO | WO 00/11168 | 3/2000 |
| WO | WO 00/73454 A1 | 7/2000 |
| WO | WO 00/55180 | 9/2000 |
| WO | WO 00/61756 | 10/2000 |
| WO | WO 01/12659 A2 | 2/2001 |
| WO | WO 01/53486 A1 | 7/2001 |
| WO | WO 01/57188 A2 | 8/2001 |
| WO | WO 01/61055 A2 | 8/2001 |
| WO | WO 02/079398 A2 | 10/2002 |

OTHER PUBLICATIONS

Zhou S, Cao JM, Tebb ZD, Ohara T, Huang HL, Omichi C, Lee MH, Kenknight BH, Chen LS, Fishbein MC, Karagueuzian HS, Chen PS. J Cardiovasc Electrophysiol Sep. 2001;12(9):1068-73.*

Lau et al (Chest Surg Clin N Am Nov. 2000 ;10(4):781-801).*

Chuman et al., Napsin A, a member of the aspartic protease family, is abundantly expressed in normal lung and kidney tissue and is expressed in lung adenocarcinoma. FEBS Letters. 1999; vol. 462:129-134.

Hirano et al., Human Tissue Distribution of TA02, Which is Homologous with a New Type of Aspartic Protease, Napsin A. Jpn. J. Cancer Res. Oct. 2000; vol. 91:1015-1021.

Mori et al., Cellular distribution of napsin (kidney-derived apsartic protease-like protein, KAP) mRNA in the kidney, lung and lymphatic organs of adult and developing mice. Arch Histol Cytol. Aug. 2001; vol. 64(3):319-27.

Rosse et al., Rapid identification of substrates for novel protease using a combinatorial peptide library. J Comb Chem. Sep.-Oct. 2000; vol. 2(5):461-6.

Schauer-Vukasinovic et al., Cloning, expression and functional characterization of rat napsin. Biochemica et Biophysica Acta. Jun. 21, 2000; vol. 1492(1):207-10.

Schauer-Vukasinovic et al., Detection of immunoreative napsin A in human urine. Biochemica et Biophysica Acta. 2000; vol. 1524:51-56.

Schauer-Vukasinovic et al., Human napsin A: expression, immunochemical detection, and tissue localization. FEBS Letters. 1999; vol. 462:135-139.

Schauer-Vukasinovic et al., Purification and characterization of active recombinant human napsin A. Eur. J. Biochem. 2000; vol. 267.

Tatnell et al., Napsins: new human aspartic proteinase distinction between two closely related genes. FEBS Letters. 1998; vol. 441:43-48.

Yan et al., Membrane-anchored aspartyl protease with Alzheimer's disease β-secretase activity. Nature. Dec. 2, 1999; vol. 402(2):533-537.

Database MEDLINE, Mar. 1998 Wang Z. et al.: "Expression and prognostic relation of cathepsin D in non-small cell lung cancer tissues and lymph nodes!" Database accession No. NLM11263354 XP002206076 *abstract*.

Athauda et al., "Structural Evidence for two Isozymic Forms and the Carbohydrate Attachment Site of Human Gastric Cathepsin E", Biochemical and Biophysical Research Communication 1990 168(2):878-885.

Amuza et al., "Human Gastric Cathepsin E Gene", J. Biol. Chem. 1992 267(3):1609-1614.

Bin et al., "Identification of Uteroglobin related Protein 1 and Macrophage Scavenger Receptor with Collagenous Structure as a Lung-Specific Ligand-Receptor Pair", J. Immunology 2003 171:924-930.

Bingle et al., "PLUNC: A novel family of candidate host defence proteins expressed in the upper airways and nasopharynx", Human Molecular Genetics 2002 11(8):937-943.

Blundell et al., "The Aspartic Proteinases", Adv. Exp. Med. Biol. 1998 436:1-13.

Clark et al., "The Secreted Protein Discovery Initiative (SPDI), a Large-Scale Effort to Identify Novel Human Secreted and Transmembrane Proteins:A Bioinformatics Assessment", Genome Research 2203 13:2265-2270.

Cook et al., "Pronapsin A and B gene expression in normal and malignant human lung and mononuclear blood cells", Biochimica et Biophysica Acta 2002 1557 10-16.

Couvreur et al., "Assignment of cathepsin E (CTSE) to human chromosome region 1q31 by in situ hybridization and analysis of somatic cell hybrids", Cytogenet Cell Genet 1990 53:137-139.

Doorbar et al., "The E1A E4 Protein of Human Papillomavirus Type 16 Associates with a Putative RNA Helicase through Sequences in Its C Terminus", J. Virology 2000 74(21): 10081-10095.

Koelsch et al., "Multiple functions of pro-parts of aspartic proteinase zymogens", FEBS Letters 1994 343:6-10.

Krop et al., "HIN-1, a putative cytokine highly expressed in normal but not cancerous mammary epithelial cells", Proc. Natl. Acad. Sci. USA 2001 98(17):9796-9801.

Niimi et al., "UGRP1, a Uteroglobin/Clara Cell Secretory Protein-Related Protein, Is a Novel Lung-Enriched Downstream Target Gene for the T/EBP/NKX2.1 Homeodomain Transcription Factor", Molecular Endocrinology 2001 15(11):2021-2036.

Niimi et al., "A Polymorphism in the Human UGRP1 Gene Promoter That Regulates Transcription Is Associated with an Increased Risk of Asthma", Am. J. Hum. Genet. 2002 70:718-725.

Niimi et al., "Cloning, expression, and chromosomal localization of the mouse gene (*Scgb3a1, alias Ugrp2*) that encodes a member of the novel uteroglobin-related protein gene family", Cyotogenet Genome Res 2002 97:120-127.

Kimura et al., "The *T/ebp* null mouse: thyroid-specific enhancer-binding protein is essential for the organogenesis of the thyroid, lung, ventral forebrain, and pituitary", Genes & Development 1996 10:60-69.

Mori et al., "Molecular cloning of a novel mouse aspartic protease-like protein that is expressed abundantly in the kidney", FEBS Letters 1997 401:218-222.

Schauer-Vukasinovic et al., "Cloning, expression and functional characterization of rat napsin", Biochimica et Biophysica Acta 2000 1492:207-210.

Shibata et al., "Disruption of structural and functional integrity of $\alpha_2$-macroglobulin by cathepsin E", Eur. J. Biochem. 2003 270:1189-1198.

Strausberg et al., "Generation and initial analysis of more than 15,000 full-length human and mouse cDNA sequences", Proc. Natl. Acad. Sci. USA 2002 99(26):16899-16903.

Takenaka et al., "Isolation of genes identified in mouse renal proximal tubule by comparing different gene expression profiles", Kidney International 1998 53:562-572.

Tatnell et al., "An alternatively spliced variant of cathepsin E in human gastric adenocarcinoma cells", Biochimica et Biophysica Acta 2003 1625:203-206.

Tatnell et al., "Molecular organization, expression and chromosomal localization of the mouse pronapsin gene", European Journal of Biochemistry 2000 267(23):6921-6931.

Wattiez et al., "Human bronchoalveolar lavage fluid protein two-dimemsional database:Study of interstitial lung diseases", Electrophoresis 2000 21:2703-2712.

Zhang et al., "Identification of Tissue-Specific Genes in Nasopharyngeal Epithelial Tissue and Differentially Expressed Genes in Nasopharyngeal Carcinoma by Suppression Subtractive Hybridization and cDNA Microarray", Genes, Chromosomes & Cancer 2003 38:80-90.

NCBI Genbank Accession No. Q920H1 [gi:20140641] Mar. 1, 2002 with Revision History.

NCBI Genbank Accession No. Q96PL1 [gi:20140698] Mar. 1, 2002 with Revision History.

NCBI Genbank Accession No. Q920D7 [gi:20140640] Mar. 1, 2002 with Revision History.

NCBI Genbank Accession No. Q96QR1 [gi:20140699] Mar. 1, 2002 with Revision History.

NCBI Genbank Accession No. AY040564 [gi:15079187] Aug. 2-15, 2001 with Revision History.

NCBI Genbank Accession No. BC029176 [gi:20809672] May 16, 2002 with Revision History.

NCBI Genbank Accession No. AF086152 [gi:3483497] Aug. 29, 1998 with Revision History.

NCBI Genbank Accession No. AF436839 [gi:33315289] Sep. 19, 2003 with Revision History.

NCBI Genbank Accession No. AY359064 [gi:37183245] Oct. 1, 2003 with Revision History.

NCBI Genbank Accession No. NM_052863 [gi:16418366] Oct. 25, 2001-Mar. 23, 2002 with Revision History.

NCBI Genbank Accession No. AC005794 [gi:3702272] Oct. 6, 1998 with Revision History.

NCBI Genbank Accession No. NP_571785 [gi:18858489] Feb. 20, 2002 with Revision History.

NCBI Genbank Accession No. NP_001900 [gi:4503143] Mar. 19, 1999-Apr. 15, 2002 with Revision History.

NCBI Genbank Accession No. NP_113858 [gi:13928928] May 2, 2001 with Revision History.

NCBI Genbank Accession No. BAA90785 [gi:6978973] Feb. 15, 2000 with Revision History.

NCBI Genbank Accession No. BAB22158 [gi:12832561] Feb. 8, 2001-Dec. 26, 2001 with Revision History.

NCBI Genbank Accession No. NP_032463 [gi:6680552] Jan. 4, 2000-Jan. 7, 2002 with Revision History.

NCBI Genbank Accession No. AAF17080 [gi:6561816] Dec. 12, 1999 with Revision History.

NCBI Genbank Accession No. NP_004842 [gi:4758754] May 7, 1999-Dec. 18, 2001 with Revision History.

NCBI Genbank Accession No. AAH17842 [gi:17389633] Dec. 6, 2001 with Revision History.

NCBI Genbank Accession No. P07339 [gi:115717] Mar. 1, 1992-Mar. 1, 2002 with Revision History.

NCBI Genbank Accession No. O09043 [gi:6016430] Jul. 15, 1999-Mar. 1, 2002 with Revision History.

NCBI Genbank Accession No. O96009 [gi:6225749] Dec. 15, 1999-Oct. 16, 2001 with Revision History.

NCBI Genbank Accession No. NM_016355 [gi:10047107] Sep. 9, 2000-Aug. 21, 2001 with Revision History.

NCBI Genbank Accession No. NM_001910 [gi:4503144] Mar. 19, 1999-Sep. 18, 2002 with Revision History.

NCBI Genbank Accession No. NP_652013 [gi:21355083] Jun. 8, 2002 with Revision History.

NCBI Genbank Accession No. NM_148964 [gi:23110951] Sep. 18, 2002 with Revision History.

NCBI Genbank Accession No. BC017842 [gi:17389632] Dec. 6, 2001 with Revision History.

NCBI Genbank Accession No. AF098484 [gi:4235424] Feb. 8, 1999 with Revision History.

NCBI Genbank Accession No. AF090386 [gi:4154286] Feb. 14, 1999 with Revision History.

NCBI Genbank Accession No. AF200345 [gi:6561817] Dec. 12, 1999 with Revision History.

NCBI Genbank Accession No. BC040958 [gi:27155062] Dec. 17, 2002 with Revision History.

NCBI Genbank Accession No. AAP36305 [gi:30584113] May 13, 2003 with Revision History.

NCBI Genbank Accession No. P24268 [gi:115720] Dec. 1, 1992-Aug. 20, 2001 with Revision History.

NCBI Genbank Accession No. AAL25709 [gi:16551119] Oct. 31, 2001 with Revision History.

NCBI Genbank Accession No. NP_473379 [gi:16905071] Nov. 12, 2001 with Revision History.

NCBI Genbank Accession No. AAL25708 [gi:16551117] Oct. 31, 2001 with Revision History.

NCBI Genbank Accession No. AAQ04562 [gi:33316004] Sep. 19, 2003 with Revision History.

NCBI Genbank Accession No. NP_473364 [gi:16876445] Nov. 9, 2001 with Revision History.

NCBI Genbank Accession No. Q96PL1 [gi:20140698] Mar. 1, 2002 with Revision History.

NCBI Genbank Accession No. Q920H1 [gi:20140641] Mar. 1, 2002 with Revision History.

NCBI Genbank Accession No. AF364078 [gi:19880273] Apr. 2, 2002 with Revision History.

NCBI Genbank Accession No. AY358595 [gi:37182311] Oct. 1, 2003 with Revision History.

NCBI Genbank Accession No. BC008429 [gi:14250057] May 30, 2001 with Revision History.

NCBI Genbank Accession No. AK127971 [gi:34535114] Sep. 9, 2003 with Revision History.

NCBI Genbank Accession No. NM_004851 [gi:4758753] May 7, 1999-Aug. 22, 2001 with Revision History.

NCBI Genbank Accession No. NM_033197 [gi:15082247] Aug. 4, 2001 with Revision History.

NCBI Genbank Accession No. AY58433 [gi:37181990] Oct. 1, 2003 with Revision History.

NCBI Genbank Accession No. XM_209141 [gi:27485250] Jan. 3, 2003 with Revision History.

NCBI Genbank Accession No. NM_198477 [gi:38348269] Nov. 15, 2003 with Revision History.

NCBI Genbank Accession No. NM_054023 [gi:16876444] Nov. 9, 2001 with Revision History.

NCBI Genbank Accession No. AY358979 [gi:37183075] Oct. 1, 2003 with Revision History.

NCBI Genbank Accession No. AF439545 [gi:33315997] Sep. 19, 2003 with Revision History.

NCBI Genbank Accession No. BC024232 [gi:18999381] Feb. 28, 2002 with Revision History.

NCBI Genbank Accession No. AF313455 [gi:16565415] Nov. 1, 2001 with Revision History.

NCBI Genbank Accession No. AC011497 [gi:6015255] Oct. 7, 1999-Jul. 14, 2002 with Revision History The Revision History for 8844110 which replaces 6015255 is provided.

NCBI Genbank Accession No. AL356798 [gi:8217849] May 24, 2000-Sep. 26, 2001 with Revision History—The Revision History for 15795413 which replaces 8217849 is provided.

NCBI Genbank Accession No. BF335657 [gi:11306405] Nov. 11, 2000 with Revision History.

* cited by examiner

METHOD OF DIAGNOSING, MONITORING, AND STAGING LUNG CANCER

This application claims the benefit of Provisional Application No. 60/086,212, filed May 21, 1998.

FIELD OF THE INVENTION

This invention relates, in part, to newly developed assays for detecting, diagnosing, monitoring, staging, and prognosticating cancers, particularly lung cancer.

BACKGROUND OF THE INVENTION

Primary lung cancer is divided into three main types including small cell lung cancer, non-small cell lung cancer, and mesothelioma. Small cell lung cancer is also called "Oat Cell" lung cancer because the cancer cells are a distinctive oat shape. There are three types of non-small cell lung cancer which are grouped together based upon similar behavior patterns and response to treatment which is different from small cell lung cancer. The three types of non-small cell lung cancer are squamous cell carcinoma, adenocarcinoma and large cell carcinoma. Squamous cell cancer is the most common type of lung cancer. It develops from the cells that line the airways. Adenocarcinoma also develops from the cells that line the airways, but it develops from a particular type of cell that produces mucus (phlegm). In large cell lung cancer, the cells appear large and rounded when viewed under a microscope. Mesothelioma is a rare type of cancer which affects the covering of the lung, the pleura. It is often caused by exposure to asbestos.

Secondary lung cancer is cancer that has started somewhere else in the body (for example, the breast or bowel) and spread to the lungs. The choice of treatment depends on where the cancer began. For example, cancer that has spread from the breast should respond to breast cancer treatments and cancer that has spread from the bowel should respond to bowel cancer treatments. The stage of a cancer provides information regarding how far a cancer has spread. Staging is important because treatment of the cancer is often decided based upon its stage. Staging is different for non-small cell versus small cell cancers of the lung.

Non-small cell cancer is divided into four stages. Stage I is very localized cancer with no cancer in the lymph nodes. In stage II, cancer has spread to the lymph nodes at the top of the affected lung. In stage III, cancer has spread near to where the cancer started. This can be to the chest wall, the covering of the lung (pleura), the middle of the chest (mediastinum) or other lymph nodes. Stage IV cancer has spread to another part of the body.

Small cell lung cancers are divided into two groups. This is because small cell lung cancer often spreads quite early. Even if spreading of the cancer is not visible on scans, it is likely that some cancer cells will have broken away and traveled through the bloodstream or lymph system. Accordingly, it is often preferred to treat small cell lung cancers as if they have spread, whether or not any secondary cancer is seen.

The two stages of small cell lung cancers are limited disease, that is cancer that can only be seen in one lung and in nearby lymph nodes, and extensive disease, that is cancer that has spread outside the lung to the chest or to other parts of the body. Because surgery is not usually used to treat small cell cancer, except in very early cases, the staging is not as important as it is with some other types of cancer. Chemotherapy with or without radiotherapy is usually preferred for treatment of small cell lung cancers. Initial scans and tests are used for comparison with later scans and test to see how well a patient is responding to treatment.

Procedures used for detecting, diagnosing, monitoring, staging and prognosticating lung cancer are of critical importance to the outcome of the patient. For example, patients diagnosed with early lung cancer generally have a much greater five-year survival rate as compared to the survival rate for patients diagnosed with distant metastasized lung cancer. New diagnostic methods which are more sensitive and specific for detecting early lung cancer are clearly needed.

Lung cancer patients are also closely monitored following initial therapy and during adjuvant therapy to determine response to therapy and to detect persistent or recurrent disease of metastasis. There is clearly a need for a lung cancer marker which is more sensitive and specific in detecting lung cancer recurrence.

Another important step in managing lung cancer is determination of the stage of the disease. Stage determination has potential prognostic value and provides criteria for designing optimal therapy. Generally, pathological staging of lung cancer is preferable over clinical staging because the former gives a more accurate prognosis. However, clinical staging would be preferred were it at least as accurate as pathological staging because it does not depend on an invasive procedure to obtain tissue for pathological evaluation. Staging of lung cancer would be improved by detecting new markers in cells, tissues or bodily fluids which could differentiate between different stages of invasion.

In the present invention, methods are provided for detecting, diagnosing, monitoring, staging and prognosticating lung cancer via six (6) Lung Specific Genes (LSGs). The six LSGs refer, among other things, to native proteins expressed by the genes comprising the polynucleotide sequences of any of SEQ ID NO: 1, 2, 3, 4, 5 or 6. In the alternative, what is meant by the six LSGs as used herein, means the native mRNAs encoded by the genes comprising any of the polynucleotide sequences of SEQ ID NO: 1, 2, 3, 4, 5 or 6 or levels of the genes comprising any of the polynucleotide sequences of SEQ ID NO: 1, 2, 3, 4, 5 or 6.

Other objects, features, advantages and aspects of the present invention will become apparent to those of skill in the art from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

SUMMARY OF THE INVENTION

Toward these ends, and others, it is an object of the present invention to provide a method for diagnosing the presence of lung cancer in a patient which comprises measuring levels of LSG in a sample of cells, tissue or bodily fluid from the patient and comparing the measured levels of LSG with levels of LSG in preferably the same cells, tissue, or bodily fluid type of a control, wherein an increase in the measured LSG levels in the patient versus levels of LSG in the control is associated with lung cancer.

Another object of the present invention is to provide a method of diagnosing metastatic lung cancer in a patient which comprises measuring LSG levels in a sample of cells, tissue, or bodily fluid from the patient and comparing the measured LSG levels with levels of LSG in preferably the same cells, tissue, or bodily fluid type of a control, wherein an increase in measured LSG levels in the patient versus levels of LSG in the control is associated with a cancer which has metastasized.

Another object of the present invention is to provide a method of staging lung cancer in a patient which comprises identifying a patient having lung cancer, measuring levels of LSG in a sample of cells, tissues, or bodily fluid obtained from the patient, and comparing the measured LSG levels with levels of LSG in preferably the same cells, tissue or bodily fluid type of a control. An increase in measured LSG levels in the patient versus LSG levels in the control can be associated with a cancer which is progressing while a decrease or equivalent level of LSG measured in the patient versus the control can be associated with a cancer which is regressing or in remission.

Another object of the present invention is to provide a method of monitoring lung cancer in a patient for the onset of metastasis. The method comprises identifying a patient having lung cancer that is not known to have metastasized, periodically measuring levels of LSG in a sample of cells, tissues, or bodily fluid obtained from the patient, and comparing the measured LSG levels with levels of LSG in preferably the same cells, tissue, or bodily fluid type of a control, wherein an increase in measured LSG levels versus control LSG levels is associated with a cancer which has metastasized.

Yet another object of the present invention is to provide a method of monitoring the change in stage of lung cancer in a patient which comprises identifying a patient having lung cancer, periodically measuring levels of LSG in a sample of cells, tissue, or bodily fluid obtained from the patient, and comparing the measured LSG levels with levels of LSG in preferably the same cells, tissues, or bodily fluid type of a control wherein an increase in measured LSG levels versus the control LSG levels is associated with a cancer which is progressing and a decrease in the measured LSG levels versus the control LSG levels is associated with a cancer which is regressing or in remission.

Other objects, features, advantages and aspects of the present invention will become apparent to those of skill in the art from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

DESCRIPTION OF THE INVENTION

The present invention relates to diagnostic assays and methods, both quantitative and qualitative for detecting, diagnosing, monitoring, staging, and prognosticating cancers by comparing levels of LSG with those of LSG in a normal human control. What is meant by "levels of LSG" as used herein, means levels of the native protein expressed by the gene comprising the polynucleotide sequence of any of SEQ ID NO: 1, 2, 3, 4, 5, or 6. In the alternative, what is meant by "levels of LSG" as used herein, means levels of the native mRNA encoded by the gene comprising any of the polynucleotide sequence of SEQ ID NO: 1, 2, 3, 4, 5, or 6 or levels of the gene comprising any of the polynucleotide sequence of SEQ ID NO: 1, 2, 3, 4, 5, or 6. Such levels are preferably measured in at least one of, cells, tissues and/or bodily fluids, including determination of normal and abnormal levels. Thus, for instance, a diagnostic assay in accordance with the invention for diagnosing over-expression of LSG protein compared to normal control bodily fluids, cells, or tissue samples may be used to diagnose the presence of cancers, including lung cancer. Any of the six LSGs may be measured alone in the methods of the invention, or all together or any combination of the six.

By "control" it is meant a human patient without cancer and/or non cancerous samples from the patient, also referred to herein as a normal human control; in the methods for diagnosing or monitoring for metastasis, control may also include samples from a human patient that is determined by reliable methods to have lung cancer which has not metastasized.

All the methods of the present invention may optionally include measuring the levels of other cancer markers as well as LSG. Other cancer markers, in addition to LSG, useful in the present invention will depend on the cancer being tested and are known to those of skill in the art.

Diagnostic Assays

The present invention provides methods for diagnosing the presence of lung cancer by analyzing for changes in levels of LSG in cells, tissues or bodily fluids compared with levels of LSG in cells, tissues or bodily fluids of preferably the same type from a normal human control, wherein an increase in levels of LSG in the patient versus the normal human control is associated with the presence of lung cancer.

Without limiting the instant invention, typically, for a quantitative diagnostic assay a positive result indicating the patient being tested has cancer is one in which cells, tissues, or bodily fluid levels of the cancer marker, such as LSG, are at least two times higher, and most preferably are at least five times higher, than in preferably the same cells, tissues, or bodily fluid of a normal human control.

The present invention also provides a method of diagnosing metastatic lung cancer in a patient having lung cancer which has not yet metastasized for the onset of metastasis. In the method of the present invention, a human cancer patient suspected of having lung cancer which may have metastasized (but which was not previously known to have metastasized) is identified. This is accomplished by a variety of means known to those of skill in the art. For example, in the case of lung cancer, patients are typically diagnosed with lung cancer following traditional detection methods.

In the present invention, determining the presence of LSG level in cells, tissues, or bodily fluid, is particularly useful for discriminating between lung cancer which has not metastasized and lung cancer which has metastasized. Existing techniques have difficulty discriminating between lung cancer which has metastasized and lung cancer which has not metastasized and proper treatment selection is often dependent upon such knowledge.

In the present invention, the cancer marker levels measured in such cells, tissues, or bodily fluid is LSG, and are compared with levels of LSG in preferably the same cells, tissue, or bodily fluid type of a normal human control. That is, if the cancer marker being observed is just LSG in serum, this level is preferably compared with the level of LSG in serum of a normal human patient. An increase in the LSG in the patient versus the normal human control is associated with lung cancer which has metastasized.

Without limiting the instant invention, typically, for a quantitative diagnostic assay a positive result indicating the cancer in the patient being tested or monitored has metastasized is one in which cells, tissues, or bodily fluid levels of the cancer marker, such as LSG, are at least two times higher, and most preferable are at least five times higher, than in preferably the same cells, tissues, or bodily fluid of a normal patient.

Staging

The invention also provides a method of staging lung cancer in a human patient.

The method comprises identifying a human patient having such cancer; analyzing a sample of cells, tissues, or bodily fluid from such patient for LSG. Then, the method compares LSG levels in such cells, tissues, or bodily fluid with levels of LSG in preferably the same cells, tissues, or bodily fluid type of a normal human control sample, wherein an increase in LSG levels in the patient versus the normal human control is associated with a cancer which is progressing and a decrease in the levels of LSG is associated with a cancer which is regressing or in remission.

Monitoring

Further provided is a method of monitoring lung cancer in a human having such cancer for the onset of metastasis. The method comprises identifying a human patient having such cancer that is not known to have metastasized; periodically analyzing a sample of cells, tissues, or bodily fluid from such patient for LSG; comparing the LSG levels in such cells, tissue, or bodily fluid with levels of LSG in preferably the same cells, tissues, or bodily fluid type of a normal human control sample, wherein an increase in LSG levels in the patient versus the normal human control is associated with a cancer which has metastasized.

Further provided by this inventions is a method of monitoring the change in stage of lung cancer in a human having such cancer. The method comprises identifying a human patient having such cancer; periodically analyzing a sample of cells, tissues, or bodily fluid from such patient for LSG; comparing the LSG levels in such cells, tissue, or bodily fluid with levels of LSG in preferably the same cells, tissues, or bodily fluid type of a normal human control sample, wherein an increase in LSG levels in the patient versus the normal human control is associated with a cancer which is progressing in stage and a decrease in the levels of LSG is associated with a cancer which is regressing in stage or in remission.

Monitoring such patient for onset of metastasis is periodic and preferably done on a quarterly basis. However, this may be more or less frequent depending on the cancer, the particular patient, and the stage of the cancer.

Assay Techniques

Assay techniques that can be used to determine levels of gene expression, such as LSG of the present invention, in a sample derived from a host are well-known to those of skill in the art. Such assay methods include radioimmunoassays, reverse transcriptase PCR (RT-PCR) assays, immunohistochemistry assays, in situ hybridization says, competitive-binding assays, Western Blot analyses and ELISA assays. Among these, ELISAs are frequently preferred to diagnose a gene's expressed protein in biological fluids.

An ELISA assay initially comprises preparing an antibody, if not readily available from a commercial source, specific to LSG, preferably a monoclonal antibody. In addition a reporter antibody generally is prepared which binds specifically to LSG. The reporter antibody is attached to a detectable reagent such as radioactive, fluorescent or enzymatic reagent, for example horseradish peroxidase enzyme or alkaline phosphatase.

To carry out the ELISA, antibody specific to LSG is incubated on a solid support, e.g., a polystyrene dish, that binds the antibody. Any free protein binding sites on the dish are then covered by incubating with a non-specific protein such as bovine serum albumin. Next, the sample to be analyzed is incubated in the dish, during which time LSG binds to the specific antibody attached to the polystyrene dish. Unbound sample is washed out with buffer. A reporter antibody specifically directed to LSG and linked to horseradish peroxidase is placed in the dish resulting in binding of the reporter antibody to any monoclonal antibody bound to LSG. Unattached reporter antibody is then washed out. Reagents for peroxidase activity, including a calorimetric substrate are then added to the dish. Immobilized peroxidase, linked to LSG antibodies, produces a colored reaction product. The amount of color developed in a given time period is proportional to the amount of LSG protein present in the sample. Quantitative results typically are obtained by reference to a standard curve.

A competition assay may be employed wherein antibodies specific to LSG attached to a solid support and labeled LSG and a sample derived from the host are passed over the solid support and the amount of label detected attached to the solid support can be correlated to a quantity of LSG in the sample.

Nucleic acid methods may be used to detect LSG mRNA as a marker for lung cancer. Polymerase chain reaction (PCR) and other nucleic acid methods, such as ligase chain reaction (LCR) and nucleic acid sequence based amplification (NASABA), can be used to detect malignant cells for diagnosis and monitoring of various malignancies. For example, reverse-transcriptase PCR (RT-PCR) is a powerful technique which can be used to detect the presence of a specific mRNA population in a complex mixture of thousands of other mRNA species. In RT-PCR, an mRNA species is first reverse transcribed to complementary DNA (cDNA) with use of the enzyme reverse transcriptase; the cDNA is then amplified as in a standard PCR reaction. RT-PCR can thus reveal by amplification the presence of a single species of mRNA. Accordingly, if the mRNA is highly specific for the cell that produces it, RT-PCR can be used to identify the presence of a specific type of cell.

Hybridization to clones or oligonucleotides arrayed on a solid support (i.e., gridding) can be used to both detect the expression of and quantitate the level of expression of that gene. In this approach, a cDNA encoding the LSG gene is fixed to a substrate. The substrate may be of any suitable type including but not limited to glass, nitrocellulose, nylon or plastic. At least a portion of the DNA encoding the LSG gene is attached to the substrate and then incubated with the analyte, which may be RNA or a complementary DNA (cDNA) copy of the RNA, isolated from the tissue of interest. Hybridization between the substrate bound DNA and the analyte can be detected and quantitated by several means including but not limited to radioactive labeling or fluorescence labeling of the analyte or a secondary molecule designed to detect the hybrid. Quantitation of the level of gene expression can be done by comparison of the intensity of the signal from the analyte compared with that determined from known standards. The standards can be obtained by in vitro transcription of the target gene, quantitating the yield, and then using that material to generate a standard curve.

The above tests can be carried out on samples derived from a variety of patients' cells, bodily fluids and/or tissue extracts (homogenates or solubilized tissue) such as from tissue biopsy and autopsy material. Bodily fluids useful in the present invention include blood, urine, saliva, or any other bodily secretion or derivative thereof. Blood can include whole blood, plasma, serum, or any derivative of blood.

EXAMPLES

The present invention is further described by the following examples. The examples are provided solely to illustrate the invention by reference to specific embodiments. These exemplifications, while illustrating certain specific aspects of the invention, do not portray the limitations or circumscribe the scope of the disclosed invention.

Example 1

LSGs

Searches were carried out and LSGs identified using the following Search Tools as part of the LIFESEQ® database available from Incyte Pharmaceuticals, Palo Alto, Calif.:
1. Library Comparison (compares one library to one other library) allows the identification of clones expressed in tumor and absent or expressed at a lower level in normal tissue.
2. Subsetting is similar to library comparison but allows the identification of clones expressed in a pool of libraries and absent or expressed at a lower level in a second pool of libraries.
3. Transcript Imaging lists all of the clones in a single library or a pool of libraries based on abundance. Individual clones can then be examined using Electronic Northerns to determine the tissue sources of their component ESTs.
4. Protein Function: Incyte has identified subsets of ESTs with a potential protein function based on homologies to known proteins. Some examples in this database include Transcription Factors and Proteases. Some lead were identified by searching in this database for clones whose component EST's showed disease specificity.

Electronic subtractions, transcript imaging and protein function searches were used to identify clones, whose component EST's were exclusively or more frequently found in libraries from specific tumors. Individual candidate clones were examined in detail by checking where each EST originated.

TABLE 1

| | LSGs | | |
|---|---|---|---|
| SEQ ID NO | Clone ID | Gene ID | |
| 1 | 126758 | 29997 | Library Comparisons |
| 2 | 2798946 | 26723 | Library Comparisons |
| 3 | 3107312 | 242842 | Transcript Imaging |
| 4 | 1472038 | 51968 | Transcript Imaging |
| 5 | 126263 | 221807 | Transcript Imaging |
| 6 | 586271 | 242745 | Transcript Imaging |

The following example was carried out using standard techniques, which are well known and routine to those of skill in the art, except where otherwise described in detail. Routine molecular biology techniques of the following example can be carried out as described in standard laboratory manuals, such as Sambrook et al., MOLECULAR CLONING: A LABORATORY MANUAL, 2nd Ed.; Cold Spring Harbor Laboratory Press, Cold Spring Harbor, N.Y. (1989).

Example 2

Relative Quantitation of Gene Expression

Real-Time quantitative PCR with fluorescent Taqman probes is a quantitation detection system utilizing the 5'-3' nuclease activity of Taq DNA polymerase. The method uses an internal fluorescent oligonucleotide probe (Taqman) labeled with a 5' reporter dye and a downstream, 3' quencher dye. During PCR, the 5'-3' nuclease activity of Taq DNA polymerase releases the reporter, whose fluorescence can then be detected by the laser detector of the Model 7700 Sequence Detection System (PE Applied Biosystems, Foster City, Calif., USA).

Amplification of an endogenous control is used to standardize the amount of sample RNA added to the reaction and normalize for Reverse Transcriptase (RT) efficiency. Either cyclophilin, glyceraldehyde-3-phosphate dehydrogenase (GAPDH) or 1BS ribosomal RNA (rRNA) is used as this endogenous control. To calculate relative quantitation between all the samples studied, the target RNA levels for one sample were used as the basis for comparative results (calibrator). Quantitation relative to the "calibrator" can be obtained using the standard curve method or the comparative method (User Bulletin #2: ABI PRISM 7700 Sequence Detection System).

The tissue distribution and the level of the target gene was evaluated for every example in normal and cancer tissue. Total RNA was extracted from normal tissues, cancer tissues, and from cancers and the corresponding matched adjacent tissues. Subsequently, first strand cDNA was prepared with reverse transcriptase and the polymerase chain reaction was done using primers and Taqman probe specific to each target gene. The results are analyzed using the ABI PRISM 7700 Sequence Detector. The absolute numbers are relative levels of expression of the target gene in a particular tissue compared to the calibrator tissue.

Comparative Examples

For comparative examples similar mRNA expression analysis for genes coding for the diagnostic markers PSA (Prostate Specific Antigen) and PLA2 (Phospholipase A2) was performed. PSA is the only cancer screening marker available in clinical laboratories. When the panel of normal pooled tissues was analyzed, PSA was expressed at very high levels in prostate, with a very low expression in breast and testis. After we analyzed more than 55 matching samples from 14 different tissues, the data corroborated the tissue specificity seen with normal tissue samples. We compared PSA expression in cancer and normal adjacent tissue for 12 matching samples of prostate tissue. The relative levels of PSA were higher in 10 cancer samples (83%). Clinical data recently obtained support the utilization of PLA2 as a staging marker for late stages of prostate cancer. Our mRNA expression data showed overexpression of the mRNA in 8 out of the 12 prostate matching samples analyzed (66%). The tissue specificity for PLA2 was not as good as the one described for PSA. In addition to prostate, also small intestine, liver, and pancreas showed high levels of mRNA expression for PLA2.

Measurement of SEQ ID NO:1; Clone ID 126758; Gene ID 29997 (Lng101)

The absolute numbers as depicted in Table 2 are relative levels of expression of LSG Lng101 (SEQ ID NO:1) in 12 normal different tissues. All the values are compared to normal testis (calibrator). These RNA samples are commercially available pools, originated by pooling samples of a particular tissue from different individuals.

TABLE 2

Relative levels of Lng101 Expression in Pooled Samples

| Tissue | NORMAL |
|---|---|
| Brain | 0 |
| Heart | 1.55 |
| Kidney | 0 |
| Liver | 0 |
| Lung | 72716 |
| Mammary Gland | 2 |
| Prostate | 0 |
| Small Intestine | 0 |
| Spleen | 0 |
| Testis | 1 |
| Thymus | 0 |
| Uterus | 0 |

The relative levels of expression in Table 2 show that mRNA expression of the LSG Lng101 (SEQ ID NO:1) is very high (72716) in lung compared with all the other normal tissues analyzed. Testis, the calibrator, with a relative expression level of 1, heart (1.55) and mammary gland (2) are the only tissues expressing the mRNA for Lng101. These results demonstrated that Lng101 mRNA expression is highly specific for lung.

The absolute numbers in Table 2 were obtained analyzing pools of samples of a particular tissue from different individuals. They can not be compared to the absolute numbers originated from RNA obtained from tissue samples of a single individual in Table 3.

The absolute numbers depicted in Table 3 are relative levels of expression of Lng101 in 44 pairs of matching samples. All the values are compared to normal testis (calibrator). A matching pair is formed by mRNA from the cancer sample for a particular tissue and mRNA from the normal adjacent sample for that same tissue from the same individual.

TABLE 3

Relative Levels of Lng101 Expression in Individual Samples

| Sample ID | Cancer Type | Tissue | Cancer | Matching Normal |
|---|---|---|---|---|
| Lng AC82 | Adenocarcinoma | Lung 1 | 17199 | 92042 |
| Lng 60XL | Adenocarcinoma | Lung 2 | 4603 | 49971 |
| Lng AC66 | Adenocarcinoma | Lung 3 | 7358 | 116907 |
| Lng AC69 | Adenocarcinoma | Lung 4 | 82953 | 47644 |
| Lng AC11 | Adenocarcinoma | Lung 5 | 37771 | 496008 |
| Lng AC39 | Adenocarcinoma | Lung 6 | 2487 | 15771 |
| Lng AC32 | Adenocarcinoma | Lung 7 | 12634 | 204254 |
| Lng SQ9X | Squamous cell carcinoma | Lung 8 | 90774 | 14462 |
| Lng SQ32 | Squamous cell carcinoma | Lung 9 | 6677 | 677567 |
| Lng SQ80 | Squamous cell carcinoma | Lung 10 | 50711 | 47151 |
| Lng SQ16 | Squamous cell carcinoma | Lung 11 | 396 | 41333 |
| Lng SQ79 | Squamous cell carcinoma | Lung 12 | 10261 | 354395 |
| Lng 47XQ | Squamous cell carcinoma | Lung 13 | 2513 | 5293 |
| Lng SQ44 | Squamous cell carcinoma | Lung 14 | 69033 | 72 |
| Lng 90X | Squamous cell carcinoma | Lung 15 | 678 | 14715 |
| Lng LC71 | Large cell carcinoma | Lung 16 | 155332 | 44762 |
| Lng LC109 | Large cell carcinoma | Lung 17 | 10191 | 322737 |

TABLE 3-continued

Relative Levels of Lng101 Expression in Individual Samples

| Sample ID | Cancer Type | Tissue | Cancer | Matching Normal |
|---|---|---|---|---|
| Lng 75XC | Metastatic from bone cancer | Lung 18 | 222033 | 165291 |
| Lng MT67 | Metastatic from renal cell cancer | Lung 19 | 189 | 35982 |
| Lng MT71 | Metastatic from melanoma | Lung 20 | 122 | 4270 |
| Bld 32XK | | Bladder 1 | 0 | 0 |
| Bld 46XK | | Bladder 2 | 0 | 0 |
| Cln AS45 | | Colon 1 | 0 | 0 |
| Cln C9XR | | Colon 2 | 0 | 0 |
| Cvx KS52 | | Cervix 1 | 0 | 0 |
| Cvx NK23 | | Cervix 2 | 0 | 0 |
| End 28XA | | Endometrium 1 | 0 | 0 |
| End 12XA | | Endometrium 2 | 0 | 0 |
| Kid 106XD | | Kidney 1 | 0 | 0 |
| Kid 107XD | | Kidney 2 | 0 | 0 |
| Liv 94XA | | Liver 1 | 0 | 0 |
| Liv 15XA | | Liver 2 | 0 | 0 |
| Mam 82XI | | Mammary 1 | 0 | 0 |
| Mam A06X | | Mammary 2 | 0 | 0 |
| Pan 71XL | | Pancreas 1 | 0 | 0 |
| Pan 77X | | Pancreas 2 | 0 | 0 |
| Pro 20XB | | Prostate 1 | 0 | 0 |
| Pro 12B | | Prostate 2 | 0 | 0 |
| SmI 21XA | | Sm. Int. 1 | 0 | 0 |
| SmI H89 | | Sm. Int. 2 | 0 | 0 |
| Sto AC44 | | Stomach | 13 | 0 |
| Tst 39X | | Testis | 4315 | 0 |
| Utr 135XO | | Uterus 1 | 0 | 0 |
| Utr 141XO | | Uterus 2 | 0 | 0 |

0 = Negative

In the analysis of matching samples, the higher levels of expression were in lung, showing a high degree of tissue specificity for this tissue. These results confirmed the tissue specificity results obtained with the panel of normal pooled samples (Table 2).

Furthermore, the level of mRNA expression in cancer samples and the isogenic normal adjacent tissue from the same individual were compared. This comparison provides an indication of specificity for the cancer stage (e.g. higher levels of mRNA expression in the cancer sample compared to the normal adjacent). Table 3 shows overexpression of LSG Lng101 in 6 lung cancer tissues compared with their respective normal adjacent (lung samples #4, 8, 10, 14, 16, and 18). There was overexpression in the cancer tissue for 30% of the lung matching samples tested (total of 20 lung matching samples).

Altogether, the high level of tissue specificity, plus the mRNA overexpression in 30% of the lung matching samples tested are demonstrative of LSG Lng101 (SEQ. ID NO:1) being a diagnostic marker for lung cancer. The amino acid sequence encoded by Lng101 (SEQ ID NO:1) is depicted in SEQ ID NO: 7.

Measurement of SEQ ID NO:3; Clone ID 3107312; Gene ID 242842 (Lng105)

The absolute numbers depicted in Table 4 are relative levels of expression of LSG Lng105 (SEQ ID NO:3) in 12 normal different tissues. All the values are compared to normal kidney (calibrator). These RNA samples are commercially available pools, originated by pooling samples of a particular tissue from different individuals.

TABLE 4

Relative levels of Lng105 Expression in Pooled Samples

| Tissue | NORMAL |
|---|---|
| Brain | 1 |
| Heart | 1.11 |
| Kidney | 558 |
| Liver | 0 |
| Lung | 9248 |
| Mammary Gland | 6 |
| Muscle | 0 |
| Prostate | 0 |
| Small Intestine | 87 |
| Testis | 50 |
| Thymus | 6 |
| Uterus | 23 |

The relative levels of expression in Table 4 show that mRNA expression of LSG Lng105 (SEQ ID NO:3) is more than 16 fold higher in the pool of normal lung (9248) compared with the next higher expressor (558 for kidney). All the other pooled tissues samples analyzed showed a very low level of expression for Lng105 (SEQ ID NO:3). These results demonstrate that mRNA expression of LSG Lng105 (SEQ ID NO:3) is highly specific for lung.

The absolute numbers in Table 4 were obtained analyzing pools of samples of a particular tissue from different individuals. They can not be compared to the absolute numbers originated from RNA obtained from tissue samples of a single individual in Table 5.

The absolute numbers depicted in Table 5 are relative levels of expression of Lng105 (SEQ ID NO:3) in 61 pairs of matching samples. All the values are compared to normal small intestine (calibrator). A matching pair is formed by mRNA from the cancer sample for a particular tissue and mRNA from the normal adjacent sample for that same tissue from the same individual.

TABLE 5

Relative Levels of Lng105 Expression in Individual Samples

| Sample ID | Cancer Type | Tissue | Cancer | Matching Normal |
|---|---|---|---|---|
| Lng AC82 | Adenocarcinoma | Lung 1 | 1278 | 742 |
| Lng C17X | Adenocarcinoma | Lung 2 | 1272 | 1948 |
| Lng 60XL | Adenocarcinoma | Lung 3 | 4345 | 2188 |
| Lng AC66 | Adenocarcinoma | Lung 4 | 1531 | 1558 |
| Lng AC69 | Adenocarcinoma | Lung 5 | 7232 | 913 |
| Lng AC88 | Adenocarcinoma | Lung 6 | 7724 | 24749 |
| Lng AC11 | Adenocarcinoma | Lung 7 | 690 | 21545 |
| Lng AC39 | Adenocarcinoma | Lung 8 | 16904 | 370 |
| Lng AC90 | Adenocarcinoma | Lung 9 | 14614 | 34 |
| Lng AC32 | Adenocarcinoma | Lung 10 | 8720 | 5061 |
| Lng SQ9X | Squamous cell carcinoma | Lung 11 | 3603 | 659 |
| Lng SQ45 | Squamous cell carcinoma | Lung 12 | 32998 | 1333 |
| Lng SQ56 | Squamous cell carcinoma | Lung 13 | 829 | 15077 |
| Lng SQ14 | Squamous cell carcinoma | Lung 14 | 7 | 6865 |
| Lng SQ32 | Squamous cell carcinoma | Lung 15 | 976 | 10227 |
| Lng SQ80 | Squamous cell carcinoma | Lung 16 | 2769 | 3554 |
| Lng SQ16 | Squamous cell carcinoma | Lung 17 | 198 | 292 |
| Lng SQ79 | Squamous cell carcinoma | Lung 18 | 1128 | 7777 |
| Lng C20X | Squamous cell carcinoma | Lung 19 | 4 | 20 |
| Lng 47XQ | Squamous cell carcinoma | Lung 20 | 276 | 117 |
| Lng SQ44 | Squamous cell carcinoma | Lung 21 | 3126 | 1 |
| Lng BR94 | Squamous cell carcinoma | Lung 22 | 709 | 6 |
| Lng 90X | Squamous cell carcinoma | Lung 23 | 258 | 590 |
| Lng LC71 | Large cell carcinoma | Lung 24 | 155332 | 44762 |
| Lng LC109 | Large cell carcinoma | Lung 25 | 34280 | 33112 |
| Lng 75XC | Metastatic from bone cancer | Lung 26 | 749 | 902 |
| Lng MT67 | Metastatic from renal cell cancer | Lung 27 | 70 | 6985 |
| Lng MT71 | Metastatic from melanoma | Lung 28 | 742 | 15992 |
| Bld 32XK | | Bladder 1 | 1 | 0 |
| Bld 46XK | | Bladder 2 | 0 | 0 |
| Cvx KS52 | | Cervix 1 | 4 | 0 |
| Cvx NK23 | | Cervix 2 | 1 | 0 |
| Cln AS45 | | Colon 1 | 0 | 1 |
| Cln C9XR | | Colon 2 | 2 | 1 |
| Cln CM67 | | Colon 3 | 0 | 0 |
| End 28XA | | Endometrium 1 | 7 | 4 |
| End 12XA | | Endometrium 2 | 0 | 0 |
| Kid 106XD | | Kidney 1 | 0 | 186 |
| Kid 107XD | | Kidney 2 | 82 | 458 |
| Kid 109XD | | Kidney 3 | 169 | 438 |
| Kid 10XD | | Kidney 4 | 21 | 186 |
| Kid 11XD | | Kidney 5 | 586 | 110 |
| Liv 94XA | | Liver 1 | 1 | 0 |
| Liv 15XA | | Liver 2 | 1 | 0 |
| Mam A06X | | Mammary 1 | 1 | 0 |
| Mam B011X | | Mammary 2 | 13 | 0 |
| Mam 12X | | Mammary 3 | 0 | 0 |
| Mam 59X | | Mammary 4 | 0 | 0 |
| Ovr 103X | | Ovary 1 | 15 | 2 |
| Pan 71XL | | Pancreas 1 | 1 | 0 |
| Pan 77X | | Pancreas 2 | 4 | 0 |
| Pro 20XB | | Prostate 1 | 1 | 1 |
| Pro 12B | | Prostate 2 | 8 | 0 |
| SmI 21XA | | Sm. Int. 1 | 4 | 0 |
| SmI H89 | | Sm. Int. 2 | 1 | 0 |
| Sto AC44 | | Stomach 1 | 0 | 2 |
| Sto AC99 | | Stomach 2 | 6 | 2 |
| Tst 39X | | Testis | 28 | 2 |
| Utr 85XU | | Uterus 1 | 3 | 2 |
| Utr 135XO | | Uterus 2 | 2 | 0 |
| Utr 141XO | | Uterus 3 | 2 | 6 |

0 = Negative

In the analysis of matching samples, the higher levels of expression were in lung showing a high degree of tissue specificity for lung tissue. These results confirm the tissue specificity results obtained with normal pooled samples (Table 4).

Furthermore, the level of mRNA expression in cancer samples and the isogenic normal adjacent tissue from the same individual were compared. This comparison provides an indication of specificity for the cancer stage (e.g. higher levels of mRNA expression in the cancer sample compared to the normal adjacent). Table 5 shows overexpression of LSG Lng105 (SEQ ID NO:3) in 13 lung cancer tissues compared with their respective normal adjacent (lung samples #1, 3, 5, 8, 9, 10, 11, 12, 20, 21, 22, 24, and 25). There is overexpression in the cancer tissue for 46% of the colon matching samples tested (total of 28 lung matching samples).

Altogether, the high level of tissue specificity, plus the mRNA overexpression in almost half of the lung matching samples tested are demonstrative of Lng105 (SEQ ID NO:3) being a diagnostic marker for lung cancer. The amino acid sequence encoded by Lng105 (SEQ ID NO:3) is depicted as SEQ ID NO:8.

Measurement of SEQ ID NO:6; Clone ID 586271; Gene ID 242745 (Lng107)

The absolute numbers depicted in Table 6 are relative levels of expression of LSG Lng107 (SEQ ID NO:6) in 12 normal different tissues. All the values are compared to normal mammary gland (calibrator). These RNA samples are commercially available pools, originated by pooling samples of a particular tissue from different individuals.

TABLE 6

Relative levels of Lng107 Expression in Pooled Samples

| Tissue | NORMAL |
| --- | --- |
| Bladder | 0 |
| Heart | 0 |
| Kidney | 0 |
| Liver | 0 |
| Lung | 23 |
| Mammary Gland | 1 |
| Muscle | 0 |
| Prostate | 0 |
| Small Intestine | 0 |
| Testis | 0 |
| Thymus | 0 |
| Uterus | 0 |

The relative levels of expression in Table 6 show that mRNA expression of LSG Lng107 (SEQ ID NO:6) is 23 fold higher in the pool of normal lung (23) compared to the expression level in the calibrator mammary gland (1). All the other tissues analyzed were negative for Lng107 (SEQ ID NO:6). These results demonstrate that Lng107 mRNA expression is highly specific for lung.

The absolute numbers in Table 6 were obtained analyzing pools of samples of a particular tissue from different individuals. They can not be compared to the absolute numbers originated from RNA obtained from tissue samples of a single individual in Table 7.

The absolute numbers depicted in Table 7 are relative levels of expression of LSG Lng107 (SEQ ID NO:6) in 57 pairs of matching samples. All the values are compared to normal prostate (calibrator). A matching pair is formed by mRNA from the cancer sample for a particular tissue and mRNA from the normal adjacent sample for that same tissue from the same individual.

TABLE 7

Relative Levels of Lng107 Expression in Individual Samples

| Sample ID | Cancer Type | Tissue | Cancer | Matching Normal |
| --- | --- | --- | --- | --- |
| Lng AC82 | Adenocarcinoma | Lung 1 | 6 | 2 |
| Lng 60XL | Adenocarcinoma | Lung 2 | 1 | 4 |
| Lng AC66 | Adenocarcinoma | Lung 3 | 1 | 0 |
| Lng AC69 | Adenocarcinoma | Lung 4 | 117 | 6 |
| Lng AC88 | Adenocarcinoma | Lung 5 | 12 | 6 |
| Lng AC11 | Adenocarcinoma | Lung 6 | 1 | 18 |
| Lng AC32 | Adenocarcinoma | Lung 7 | 4 | 2 |
| Lng AC39 | Adenocarcinoma | Lung 8 | 2 | 1 |
| Lng AC90 | Adenocarcinoma | Lung 9 | 1 | 0 |
| Lng SQ9X | Squamous cell carcinoma | Lung 10 | 7 | 0 |
| Lng SQ45 | Squamous cell carcinoma | Lung 11 | 45 | 1 |
| Lng SQ56 | Squamous cell carcinoma | Lung 12 | 1 | 23 |
| Lng SQ16 | Squamous cell carcinoma | Lung 13 | 0 | 0 |
| Lng SQ32 | Squamous cell carcinoma | Lung 14 | 9 | 5 |
| Lng SQ80 | Squamous cell carcinoma | Lung 15 | 2 | 0 |
| Lng SQ79 | Squamous cell carcinoma | Lung 16 | 5 | 11 |
| Lng C20X | Squamous cell carcinoma | Lung 17 | 0 | 0 |
| Lng 47XQ | Squamous cell carcinoma | Lung 18 | 1 | 0 |
| Lng SQ44 | Squamous cell carcinoma | Lung 19 | 1 | 0 |
| Lng BR94 | Squamous cell carcinoma | Lung 20 | 1 | 0 |
| Lng 90X | Squamous cell carcinoma | Lung 21 | 0 | 13 |
| Lng LC71 | Large cell carcinoma | Lung 22 | 31 | 12 |
| Lng LC109 | Large cell carcinoma | Lung 23 | 1 | 83 |
| Lng 75XC | Metastatic from bone cancer | Lung 24 | 2 | 4 |
| Lng MT67 | Metastatic from renal cell cancer | Lung 25 | 0 | 1 |
| Lng MT71 | Metastatic from melanoma | Lung 26 | 0 | 24 |
| Bld 32XK | | Bladder 1 | 0 | 0 |
| Bld 46XK | | Bladder 2 | 0 | 0 |
| Cln AS45 | | Colon 1 | 0 | 0 |
| Cln C9XR | | Colon 2 | 0 | 0 |
| Cvx KS52 | | Cervix 1 | 0 | 0 |
| Cvx NK23 | | Cervix 2 | 0 | 0 |
| End 28XA | | Endometrium 1 | 7 | 0 |
| End 12XA | | Endometrium 2 | 0 | 0 |
| End 68X | | Endometrium 3 | 3 | 2 |
| End 8XA | | Endometrium 4 | 0 | 0 |
| Kid 106XD | | Kidney 1 | 0 | 0 |
| Kid 107XD | | Kidney 2 | 0 | 0 |
| Liv 94XA | | Liver 1 | 0 | 0 |
| Liv 15XA | | Liver 2 | 0 | 0 |
| Mam A06X | | Mammary 1 | 0 | 0 |
| Mam B011X | | Mammary 2 | 116 | 0 |
| Mam 47XP | | Mammary 3 | 0 | 0 |
| Mam 59X | | Mammary 4 | 1 | 0 |
| Ovr 103X | | Ovary 1 | 0 | 0 |
| Pan 71XL | | Pancreas 1 | 0 | 0 |
| Pan 77X | | Pancreas 2 | 0 | 0 |
| Pro 20XB | | Prostate 1 | 0 | 0 |
| Pro 12B | | Prostate 2 | 0 | 0 |
| SmI 21XA | | Sm. Int. 1 | 0 | 0 |
| SmI H89 | | Sm. Int. 2 | 0 | 0 |
| Sto AC44 | | Stomach 1 | 0 | 0 |
| Sto MT54 | | Stomach 2 | 0 | 0 |
| Sto TA73 | | Stomach 3 | 1 | 1 |
| Tst 39X | | Testis | 0 | 0 |
| Utr 135XO | | Uterus 1 | 0 | 0 |
| Utr 141XO | | Uterus 2 | 0 | 0 |

0 = Negative

In the analysis of matching samples, the higher level of expression was in lung, showing a high degree of tissue specificity for this tissue. These results confirm the tissue specificity results obtained with normal pooled samples (Table 6).

Furthermore, the level of mRNA expression in cancer samples and the isogenic normal adjacent tissue from the same individual were compared. This comparison provides an indication of specificity for the cancer stage (e.g. higher levels of mRNA expression in the cancer sample compared to the normal adjacent). Table 7 shows overexpression of LSG Lng107 (SEQ ID NO:6) in 15 lung cancer tissues compared with their respective normal adjacent (lung samples #1, 3, 4, 5, 7, 8, 9, 10, 11, 14, 15, 18, 19, 20, and 22). There is overexpression in the cancer tissue for 57% of the lung matching samples tested (total of 26 lung matching samples).

Altogether, the high level of tissue specificity, plus the mRNA overexpression in more than half of the lung matching samples tested are demonstrative of Lng107 being a diagnostic marker for lung cancer. The amino acid sequence encoded by Lng107 is depicted in SEQ ID NO:9.

What is claimed is:

1. A method for detecting the presence of lung cancer in a patient comprising:
    (a) measuring levels of a polynucleotide comprising SEQ ID NO: 2, 4, 5 or 6 in a sample of cells, tissue or bodily fluid obtained from the patient; and
    (b) comparing the measured levels of the polynucleotide in the patient with levels of the polynucleotide in a sample of cells, tissue or bodily fluid obtained from a normal control, wherein an increase in levels of the polynucleotide in the patient as compared to levels of the polynucleotide in the normal control is associated with the presence of lung cancer.

2. The method of claim 1 wherein the polynucleotide comprises SEQ ID NO:2.

3. The method of claim 1 wherein the polynucleotide comprises SEQ ID NO:4.

4. The method of claim 1 wherein the polynucleotide comprises SEQ ID NO:5.

5. The method of claim 1 wherein the polynucleotide comprises SEQ ID NO:6.

6. The method of claim 1 wherein the sample is cells.

7. The method of claim 1 wherein the sample is a tissue.

8. The method of claim 1 wherein the sample is a bodily fluid.

9. The method of claim 8 wherein the bodily fluid sample is selected from the group comprising blood, urine, saliva and bodily secretions.

10. The method of claim 9 wherein the blood sample is selected from the group comprising whole blood, plasma and serum.

11. The method of claim 8 wherein the bodily fluid sample is blood.

12. The method of claim 8 wherein the bodily fluid sample is urine.

13. The method of claim 8 wherein the bodily fluid sample is saliva.

14. The method of claim 8 wherein the bodily fluid sample is a bodily secretion.

15. The method of claim 9 wherein the blood sample is whole blood.

16. The method of claim 9 wherein the blood sample is plasma.

17. The method of claim 9 wherein the blood sample is serum.

* * * * *

SEQUENCE LISTING

<160> NUMBER OF SEQ ID NOS: 9

<210> SEQ ID NO 1
<211> LENGTH: 507
<212> TYPE: DNA
<213> ORGANISM: Homo sapiens

<400> SEQUENCE: 1

```
ggcaagtgga accactggct tggtggattt tgctagattt ttctgatttt taaactcctg      60
aaaaatatcc cagataactg tcatgaagct ggtaactatc ttcctgctgg tgaccatcag     120
cctttgtagt tactctgcta ctgccttcct catcaacaaa gtgccccttc ctgttgacaa     180
gttggcacct ttacctctgg acaacattct tcccttatg  gatccattaa agcttcttct    240
gaaaactctg ggcatttctg ttgagcacct tgtggagggg ctaaggaagt gtgtaaatga     300
gctgggacca gaggcttctg aagctgtgaa gaaactgctg gaggcgctat cacacttggt     360
gtgacatcaa gataaagagc ggaggtggat ggggatggaa gatgatgctc ctatcctccc     420
tgcctgaaac ctgttctacc aattatagat caaatgccct aaaatgtagt gacccgtgaa     480
aaggacaaat aaagcaatga atacatt                                         507
```

<210> SEQ ID NO 2
<211> LENGTH: 1680
<212> TYPE: DNA
<213> ORGANISM: Homo sapiens

<400> SEQUENCE: 2

```
ggtgtgcagg atataaggtt ggacttccag acccactgcc cgggagagga grggagcggg      60
ccgaggactc cagcgtgccc aggtctggca tcctgcactt gctgccctct gacacctggg     120
aagatggccg gcccgtggac cttcaccctt ctctgtggtt tgctggcagc caccttgatc     180
caagccaccc tcagtcccac tgcagttctc atcctcggcc caaaagtcat caaagaaaag     240
ctgacacagg agctgaagga ccacaacgcc accagcatcc tgcagcagct gccgctgctc     300
agtgccatgc gggaaaagcc agccggagga tccctgtgct gggcagcctg gtgaacaccg     360
tcctgaagca catcatctgg ctgaaggtca tcacagctaa catcctccag ctgcaggtga     420
agccctcggc caatgaccag gagctgctag tcaagatccc cctggacatg gtggctggat     480
tcaacacgcc cctggtcaag accatcgtgg agttccacat gacgactgag gcccaagcca     540
ccatccgcat ggacaccagt gcaagtggcc ccacccgcct ggtcctcagt gactgtgcca     600
ccagccatgg gagcctgcgc atccaactgc tgcataagct ctccttcctg gtgaacgcct     660
tagctaagca ggtcatgaac ctcctagtgc catccctgcc caatctagtg aaaaaccagc     720
tgtgtcccgt gatcgaggct tccttcaatg gcatgtatgc agacctcctg cagctggtga     780
aggtgcccat ttccctcagc attgaccgtc tggagtttga ccttctgtat cctgccatca     840
agggtgacac cattcagctc tacctggggg ccaagttgtt ggactcacag ggaaaggtga     900
```

-continued

| | | | |
|---|---|---|---|
| ccaagtggtt caataactct gcagcttccc tgacaatgcc caccctggac aacatcccgt | 960 |
| tcagcctcat cgtgagtcag gacgtggtga aagctgcagt ggctgctgtg ctctctccag | 1020 |
| aagaattcat ggtcctgttg gactctgtgc ttcctgagag tgcccatcgg ctgaagtcaa | 1080 |
| gcatcgggct gatcaatgaa aaggctgcag ataagctggg atctacccag atcgtgaaga | 1140 |
| tcctaactca ggacactccc gagttttta tagaccaagg ccatgccaag gtggcccaac | 1200 |
| tgatcgtgct ggaagtgttt ccctccagtg aagccctccg ccctttgttc accctgggca | 1260 |
| tcgaagccag ctcggaagct cagttttaca ccaaaggtga ccaacttata ctcaacttga | 1320 |
| ataacatcag ctctgatcgg atccagctga tgaactctgg gattggctgg ttccaacctg | 1380 |
| atgttctgaa aaacatcatc actgagatca tccactccat cctgctgccg aaccagaatg | 1440 |
| gcaaattaag atctggggtc ccagtgtcat tggtgaaggc cttgggattc gaggcagctg | 1500 |
| agtcctcact gaccaaggat gcccttgtgc ttactccagc ctccttgtgg aaacccagct | 1560 |
| ctcctgtctc ccagtgaaga cttggatggc agccatcagg gaaggctggg tcccagctgg | 1620 |
| gagtatgggt gtgagctcta tagaccatcc ctctctgcaa tcaataaaca cttgcctgtg | 1680 |

<210> SEQ ID NO 3
<211> LENGTH: 2060
<212> TYPE: DNA
<213> ORGANISM: Homo sapiens

<400> SEQUENCE: 3

| | | | |
|---|---|---|---|
| cttgagagct ctcaaatact tggtcatgga tgaagccgac cgaatactga atatggattt | 60 |
| tgagacagag gttgacaagc ctcgagatcg gaaaacattc ctcttctctg ccaccatgac | 120 |
| caagaaggtt caaaaacttc agcgagcagc tctgaagaat cctgtgaaat gtgccgtttc | 180 |
| ctctaaatac cagacagttg aaaaattaca gcaatattat atttttattc cctctaaatt | 240 |
| caaggatacc tacctggttt atattctaaa tgaattggct ggaaactcct ttatgatatt | 300 |
| ctgcagcacc tgtaataata cccagagaac agctttgcta ctgcgaaatc ttggcttcac | 360 |
| tgccatcccc ctccatggac aaatgagtca gagtaagcgc ctaggatccc ttaataagtt | 420 |
| taaggccaag gcccgttcca ttcttctagc aactgacgtt gccagccgag gtttggacat | 480 |
| acctcatgta gatgtggttg tcaactttga cattcctacc cattccaagg attacatcca | 540 |
| tcgagtaggt cgaacagcta gagctgggcg ctccggaaag gctattactt ttgtcacaca | 600 |
| gtatgatgtg gaactcttcc agcgcataga acacttaatt gggaagaaac taccaggttt | 660 |
| tccaacacag gatgatgagg ttatgatgct gacagaacgc gtccccagcg atgtctccac | 720 |
| caccgctgct gcaaccctg ctgctgctgc tgcctctgct gaatgtggag ccttccgggg | 780 |
| ccacactgat ccgcatccct cttcatcgag tccaacctgg acgcaggacc ctgaacctac | 840 |
| tgagggatg gagagaacca gcagagctcc ccagttggg ggcccatcc cctggggaca | 900 |
| agcccatctt cgtacctctc tcgaactaca gggatgtgca gtattttggg gaaattgggc | 960 |
| tgggaacgcc tccacaaaac ttcactgttg cctttgacac tggctcctcc aatctctggg | 1020 |
| tcccgtccag gagatgccac ttcttcagtg tgccctgctg gttacaccac cgatttgatc | 1080 |
| ccaaagcctc tagctccttc caggccaatg ggaccaagtt tgccattcaa tatggaactg | 1140 |
| ggcgggtaga tggaatcctg agcgaggaca agctgactat tggtggaatc aagggtgcat | 1200 |
| cagtgatttt cggggaggct ctctgggagc ccagcctggt cttcgctttt gcccatttg | 1260 |
| atgggatatt gggcctcggt tttcccattc tgtctgtgga aggagttcgg ccccgatgg | 1320 |
| atgtactggt ggagcagggg ctattggata agcctgtctt ctccttttac ctcaacaggg | 1380 |

-continued

| | |
|---|---|
| accctgaaga gcctgatgga ggagagctgg tcctgggggg ctcggacccg gcacactaca | 1440 |
| tcccacccct caccttcgtg ccagtcacgg tccctgccta ctggcagatc cacatggagc | 1500 |
| gtgtgaaggt gggcccaggg ctgactctct gtgccaaggg ctgtgctgcc atcctggata | 1560 |
| cgggcacgtc cctcatcaca ggacccactg aggagatccg ggccctgcat gcagccattg | 1620 |
| ggggaatccc cttgctggct ggggagtaca tcatcctgtg ctcggaaatc ccaaagctcc | 1680 |
| ccgcagtctc cttccttctt ggggggtct ggtttaacct cacggcccat gattacgtca | 1740 |
| tccagactac tcgaaatggc gtccgcctct gcttgtccgg tttccaggcc ctggatgtcc | 1800 |
| ctccgcctgc agggcccttc tggatcctcg gtgacgtctt cttggggacg tatgtggccg | 1860 |
| tcttcgaccg cggggacatg aagagcagcc ccgggtggg cctggcgcgc gctcgcactc | 1920 |
| gcggagcgga cctcggatgg ggagagactg cgcaggcgca gttccccggg tgacgcccaa | 1980 |
| gtgaagcgca tgcgcagcgg gtggtcgcgg aggtcctgct acccagtaaa aatccactat | 2040 |
| ttccattgaa aaaaaaaaa | 2060 |

<210> SEQ ID NO 4
<211> LENGTH: 315
<212> TYPE: DNA
<213> ORGANISM: Homo sapiens

<400> SEQUENCE: 4

| | |
|---|---|
| taaacactga ctcagatttt aagaaataac ttttgagaaa tagaacaaat gaaatcagtt | 60 |
| tctccaccac ttaagtatat ctcttagaga tctacagcct ccctttaggg gacatacaaa | 120 |
| gtcagttgtg ttgcctttgt tgagtccac cttatattca gtaggtatg actacaaatt | 180 |
| ttgaaaatag attgtcacac aataaactgg agtttatgga aacatcagta gaaggaaata | 240 |
| caacattcca tcccttttaca gagatcattt acttgcaact caggataatt tgtcatgtgt | 300 |
| attatctact tatgc | 315 |

<210> SEQ ID NO 5
<211> LENGTH: 895
<212> TYPE: DNA
<213> ORGANISM: Homo sapiens

<400> SEQUENCE: 5

| | |
|---|---|
| ctaatctgtt acgtaacagc aagacagcgt cacctcacct gttctcgccc tcaaatggga | 60 |
| acgctggcct gggactaaag catagaccac caggctgagt atcctgacct gagtcatccc | 120 |
| cagggatcag gagcctccag cagggaacct tccattatat tcttcaagca acttacagct | 180 |
| gcaccgacag ttgcgatgaa agttctaatc tcttccctcc tcctgttgct gccactaatg | 240 |
| ctgatgtcca tggtctctag cagcctgaat ccaggggtcg ccagaggcca cagggaccga | 300 |
| ggccaggctt ctaggagatg gctccaggaa ggcggccaag aatgtgagtg caaagattgg | 360 |
| ttcctgagag ccccgagaag aaaattcatg acagtgtctg ggctgccaaa gaagcagtgc | 420 |
| ccctgtgatc atttcaaggg caatgtgaag aaaacaagac accaaaggca ccacagaaag | 480 |
| ccaaacaagc attccagagc ctgccagcaa tttctcaaac aatgtcagct aagaagcttt | 540 |
| gctctgcctt tgtaggagct ctgagcgccc actcttccaa ttaaacattc tcagccaaga | 600 |
| agacagtgag cacacctacc agacactctt cttctcccac ctcactctcc cactgtaccc | 660 |
| accccctaaat cattccagtg ctctcaaaaa gcatgttttt caagatcatt ttgtttgttg | 720 |
| ctctctctag tgtcttcttc tctcgtcagt cttagcctgt gccctcccct tacccaggct | 780 |

```
taggcttaat tacctgaaag attccaggaa actgtagctt cctagctagt gtcatttaac      840
cttaaatgca atcaggaaag tagcaaacag aagtcaataa atatttttaa atgtc           895
```

<210> SEQ ID NO 6
<211> LENGTH: 543
<212> TYPE: DNA
<213> ORGANISM: Homo sapiens

<400> SEQUENCE: 6

```
ccggcgctgg aggggcgagg accgggtata agaagcctcg tggccttgcc cgggcagccg       60
caggttcccc gcgcgccccg agcccccgcg ccatgaagct cgccgccctc ctggggctct      120
gcgtggccct gtcctgcagc tccgctgctg ctttcttagt gggctcggcc aagcctgtgg      180
cccagcctgt cgctgcgctg agtcggcgg cggaggccgg ggccgggacc ctggccaacc      240
ccctcggcac cctcaacccg ctgaagctcc tgctgagcag cctgggcatc cccgtgaacc      300
acctcataga gggctcccag aagtgtgtgg ctgagctggg tccccaggcc gtgggggccg      360
tgaaggccct gaaggccctg ctgggggccc tgacagtgtt tggctgagcc gagactggag      420
catctacacc tgaggacaag acgctgccca cccgcgaggg ctgaaaaccc cgccgcgggg      480
aggaccgtcc atccccttcc cccggcccct ctcaataaac gtggttaaga gcaaaaaaaa      540
aaa                                                                    543
```

<210> SEQ ID NO 7
<211> LENGTH: 93
<212> TYPE: PRT
<213> ORGANISM: Homo sapiens

<400> SEQUENCE: 7

```
Met Lys Leu Val Thr Ile Phe Leu Leu Val Thr Ile Ser Leu Cys Ser
  1               5                  10                  15

Tyr Ser Ala Thr Ala Phe Leu Ile Asn Lys Val Pro Leu Pro Val Asp
             20                  25                  30

Lys Leu Ala Pro Leu Pro Leu Asp Asn Ile Leu Pro Phe Met Asp Pro
         35                  40                  45

Leu Lys Leu Leu Leu Lys Thr Leu Gly Ile Ser Val Glu His Leu Val
 50                  55                  60

Glu Gly Leu Arg Lys Cys Val Asn Glu Leu Gly Pro Glu Ala Ser Glu
 65                  70                  75                  80

Ala Val Lys Lys Leu Leu Glu Ala Leu Ser His Leu Val
             85                  90
```

<210> SEQ ID NO 8
<211> LENGTH: 420
<212> TYPE: PRT
<213> ORGANISM: Homo sapiens

<400> SEQUENCE: 8

```
Met Ser Pro Pro Leu Leu Gln Pro Leu Leu Leu Leu Leu Pro Leu
  1               5                  10                  15

Leu Asn Val Glu Pro Ser Gly Ala Thr Leu Ile Arg Ile Pro Leu His
             20                  25                  30

Arg Val Gln Pro Gly Arg Arg Thr Leu Asn Leu Leu Arg Gly Trp Arg
         35                  40                  45

Glu Pro Ala Glu Leu Pro Lys Leu Gly Ala Pro Ser Pro Gly Asp Lys
 50                  55                  60

Pro Ile Phe Val Pro Leu Ser Asn Tyr Arg Asp Val Gln Tyr Phe Gly
```

```
                65                  70                  75                  80
Glu Ile Gly Leu Gly Thr Pro Pro Gln Asn Phe Thr Val Ala Phe Asp
                        85                  90                  95

Thr Gly Ser Ser Asn Leu Trp Val Pro Ser Arg Arg Cys His Phe Phe
                100                 105                 110

Ser Val Pro Cys Trp Leu His His Arg Phe Asp Pro Lys Ala Ser Ser
            115                 120                 125

Ser Phe Gln Ala Asn Gly Thr Lys Phe Ala Ile Gln Tyr Gly Thr Gly
        130                 135                 140

Arg Val Asp Gly Ile Leu Ser Glu Asp Lys Leu Thr Ile Gly Gly Ile
145                 150                 155                 160

Lys Gly Ala Ser Val Ile Phe Gly Glu Ala Leu Trp Glu Pro Ser Leu
                165                 170                 175

Val Phe Ala Phe Ala His Phe Asp Gly Ile Leu Gly Leu Gly Phe Pro
                180                 185                 190

Ile Leu Ser Val Glu Gly Val Arg Pro Pro Met Asp Val Leu Val Glu
            195                 200                 205

Gln Gly Leu Leu Asp Lys Pro Val Phe Ser Phe Tyr Leu Asn Arg Asp
        210                 215                 220

Pro Glu Glu Pro Asp Gly Gly Glu Leu Val Leu Gly Gly Ser Asp Pro
225                 230                 235                 240

Ala His Tyr Ile Pro Pro Leu Thr Phe Val Pro Val Thr Val Pro Ala
                245                 250                 255

Tyr Trp Gln Ile His Met Glu Arg Val Lys Val Gly Pro Gly Leu Thr
                260                 265                 270

Leu Cys Ala Lys Gly Cys Ala Ala Ile Leu Asp Thr Gly Thr Ser Leu
            275                 280                 285

Ile Thr Gly Pro Thr Glu Glu Ile Arg Ala Leu His Ala Ala Ile Gly
        290                 295                 300

Gly Ile Pro Leu Leu Ala Gly Glu Tyr Ile Ile Leu Cys Ser Glu Ile
305                 310                 315                 320

Pro Lys Leu Pro Ala Val Ser Phe Leu Leu Gly Gly Val Trp Phe Asn
                325                 330                 335

Leu Thr Ala His Asp Tyr Val Ile Gln Thr Thr Arg Asn Gly Val Arg
                340                 345                 350

Leu Cys Leu Ser Gly Phe Gln Ala Leu Asp Val Pro Pro Pro Ala Gly
            355                 360                 365

Pro Phe Trp Ile Leu Gly Asp Val Phe Leu Gly Thr Tyr Val Ala Val
        370                 375                 380

Phe Asp Arg Gly Asp Met Lys Ser Ser Ala Arg Val Gly Leu Ala Arg
385                 390                 395                 400

Ala Arg Thr Arg Gly Ala Asp Leu Gly Trp Gly Glu Thr Ala Gln Ala
                405                 410                 415

Gln Phe Pro Gly
            420

<210> SEQ ID NO 9
<211> LENGTH: 104
<212> TYPE: PRT
<213> ORGANISM: Homo sapiens

<400> SEQUENCE: 9

Met Lys Leu Ala Ala Leu Leu Gly Leu Cys Val Ala Leu Ser Cys Ser
  1               5                  10                  15
```

-continued

```
Ser Ala Ala Ala Phe Leu Val Gly Ser Ala Lys Pro Val Ala Gln Pro
            20                  25                  30

Val Ala Ala Leu Glu Ser Ala Ala Glu Ala Gly Ala Gly Thr Leu Ala
            35                  40                  45

Asn Pro Leu Gly Thr Leu Asn Pro Leu Lys Leu Leu Leu Ser Ser Leu
        50                  55                  60

Gly Ile Pro Val Asn His Leu Ile Glu Gly Ser Gln Lys Cys Val Ala
65                  70                  75                  80

Glu Leu Gly Pro Gln Ala Val Gly Ala Val Lys Ala Leu Lys Ala Leu
                85                  90                  95

Leu Gly Ala Leu Thr Val Phe Gly
            100
```